(12) United States Patent
Piantoni et al.

(10) Patent No.: US 10,610,419 B2
(45) Date of Patent: Apr. 7, 2020

(54) MACHINE AND METHOD FOR MAKING ABSORBENT SANITARY ARTICLES

(71) Applicant: GDM S.p.A., Bologna (IT)

(72) Inventors: Matteo Piantoni, Albino (IT); Valerio Soli, Bologna (IT)

(73) Assignee: GDM S.P.A., Bologna (IT)

( * ) Notice: Subject to any disclaimer, the term of this patent is extended or adjusted under 35 U.S.C. 154(b) by 1160 days.

(21) Appl. No.: 14/784,403

(22) PCT Filed: Apr. 8, 2014

(86) PCT No.: PCT/IB2014/060525
§ 371 (c)(1),
(2) Date: Oct. 14, 2015

(87) PCT Pub. No.: WO2014/170796
PCT Pub. Date: Oct. 23, 2014

(65) Prior Publication Data
US 2018/0303679 A1    Oct. 25, 2018

(30) Foreign Application Priority Data

Apr. 17, 2013 (IT) .............................. BO2013A0173

(51) Int. Cl.
*G01B 15/00* (2006.01)
*A61F 13/15* (2006.01)
*G01N 22/02* (2006.01)

(52) U.S. Cl.
CPC .. *A61F 13/15772* (2013.01); *A61F 13/15658* (2013.01); *A61F 13/15764* (2013.01); *A61F 13/15804* (2013.01); *G01N 22/02* (2013.01)

(58) Field of Classification Search
CPC .......... A61F 13/15772; A61F 13/15764; A61F 13/15804; A61F 13/15658; G01N 22/02
See application file for complete search history.

(56) References Cited

U.S. PATENT DOCUMENTS 5,359,525 A  * 10/1994  Weyenberg ....... A61F 13/15772
                                                      356/429
6,476,619 B1    11/2002  Moshe et al.
(Continued)

FOREIGN PATENT DOCUMENTS

| CN | 101903000 A | 12/2010 |
|----|-------------|---------|
| CN | 101909563 A | 12/2010 |

(Continued)

OTHER PUBLICATIONS

Kokubo et al., JP 2008-154964 A, machine translation Jul. 10, 2008 (Year: 2008).*

(Continued)

*Primary Examiner* — Galen H Hauth
(74) *Attorney, Agent, or Firm* — Shuttleworth & Ingersoll, PLC; Timothy J. Klima (57) ABSTRACT

A machine for making absorbent sanitary articles which includes an absorbent pad in turn including one or more absorbent materials; the machine includes a line for feeding at least one continuous web of impermeable material and at least one unit for forming and applying a succession of absorbent pads along the continuous web of impermeable material and a device for detecting at least one between the weight, density profile (or weight profile) parameters of at least one of the absorbent materials defining the absorbent pad; the detecting device including at least one microwave resonator.

9 Claims, 4 Drawing Sheets (56) References Cited

U.S. PATENT DOCUMENTS

| | | | |
|---|---|---|---|
| 2005/0179443 A1* | 8/2005 | Peters | D01G 31/006 |
| | | | 324/636 |
| 2009/0178755 A1 | 7/2009 | Hornung et al. | |
| 2010/0176818 A1* | 7/2010 | Herrmann | A24D 3/0295 |
| | | | 324/640 |
| 2011/0003673 A1 | 1/2011 | Piantoni et al. | |
| 2014/0043045 A1* | 2/2014 | Zaage | A24D 3/0295 |
| | | | 324/635 |

FOREIGN PATENT DOCUMENTS

| | | | |
|---|---|---|---|
| EP | 1366734 A1 | | 12/2003 |
| EP | 2345395 A1 | | 7/2011 |
| JP | 2008154964 A | * | 7/2008 |
| JP | 2012011235 A | | 1/2012 |
| WO | WO0012974 A1 | | 3/2000 |
| WO | WO2009/073849 A1 | | 6/2009 |

OTHER PUBLICATIONS

International Search Report and Written Opinion dated Jun. 4, 2014 for related PCT Application No. PCT/IB2014/060525.
European Office Action dated Apr. 12, 2017 for counterpart European Patent Application No. 14722355.6.
European Office Action dated Apr. 26, 2018 for counterpart European Patent Application No. 14722355.6.
Chinese Office Action dated Feb. 22, 2019 for counterpart Chinese Patent Application No. 201480034077.9.
Japanese Office Action dated Apr. 3, 2018 for counterpart Japanese Patent Application No. 2016-508258.
Chinese Office Action dated May 17, 2018 for counterpart Chinese Patent Application No. 201480034077.9.

* cited by examiner

MACHINE AND METHOD FOR MAKING ABSORBENT SANITARY ARTICLES

This application is the National Phase of International Application PCT/IB2014/060525 filed Apr. 8, 2014 which designated the U.S. and that International Application was published under PCT Article 21(2) in English.

This application claims priority to Italian Patent Application No. BO2013A000173 filed Apr. 17, 2013, which application is incorporated by reference herein.

TECHNICAL FIELD

This invention relates to a machine and a method for making absorbent sanitary articles.

BACKGROUND ART

Typically, absorbent sanitary articles comprise an impermeable layer, for example of polyethylene, a layer of non-woven fabric permeable to liquids and an absorbent pad sandwiched therebetween.

These are the basic components of an absorbent article.

In addition to these basic components, absorbent articles comprise further accessory components, such as, for example, elastic bands, faecal barriers and side tabs, which vary the complexity of the structure and production process of the absorbent articles to different degrees.

Prior art machines for making absorbent sanitary articles comprise a line for feeding a continuous web of impermeable material along which there are a plurality of operating units which provide the continuous web with the basic and accessory components needed to make up the finished absorbent article.

Along the feed line, at the operating units, there are a plurality of inspection stations designed to check that the basic and accessory components meet respective quality parameters.

Special attention is reserved for inspection of the absorbent pad of the absorbent article.

Generally speaking, the absorbent pad is made mainly from natural fibres (known as "fluff") uniformly blended with superabsorbent polymer material ("SAP")

The absorbent pad may also comprise one or more discrete absorbent layers made mainly or exclusively of superabsorbent polymer material ("SAP").

In order to check the quality of the absorbent pad of each absorbent article, the prior art teaches the use of an inductive sensor capable of detecting the weight and density profile of the entire pad.

Owing to the high speeds of the feed line, however, sensors of this kind tend to be unstable during machine operation and need to be calibrated frequently.

Moreover, inductive sensors do not allow the weight and density profile of individual absorbent materials making up the pad, such as fluff and "SAP" to be detected distinctly from each other, because sensors of this kind are unable to distinguish each single absorbent material used to make the pad.

With the development of absorbent pads containing less and less fluff and more and more "SAP" the margin of error relating to the contribution, in weight, of the fluff and of the "SAP" in the pad, is more and more reduced.

For this reason, it is very important to be able to check the weight and density profile (or weight profile) of each single material making up the absorbent pad.

AIM OF THE INVENTION

It is an objective to provide a machine and a method for making absorbent sanitary articles, as disclosed herein, and which overcome the above mentioned disadvantages of the prior art.

BRIEF DESCRIPTION OF THE DRAWINGS

The invention will now be described with reference to the accompanying drawings which illustrate non-limiting embodiments of it and in which.

DETAILED DESCRIPTION OF PREFERRED EMBODIMENTS OF THE INVENTION

Figure 1:
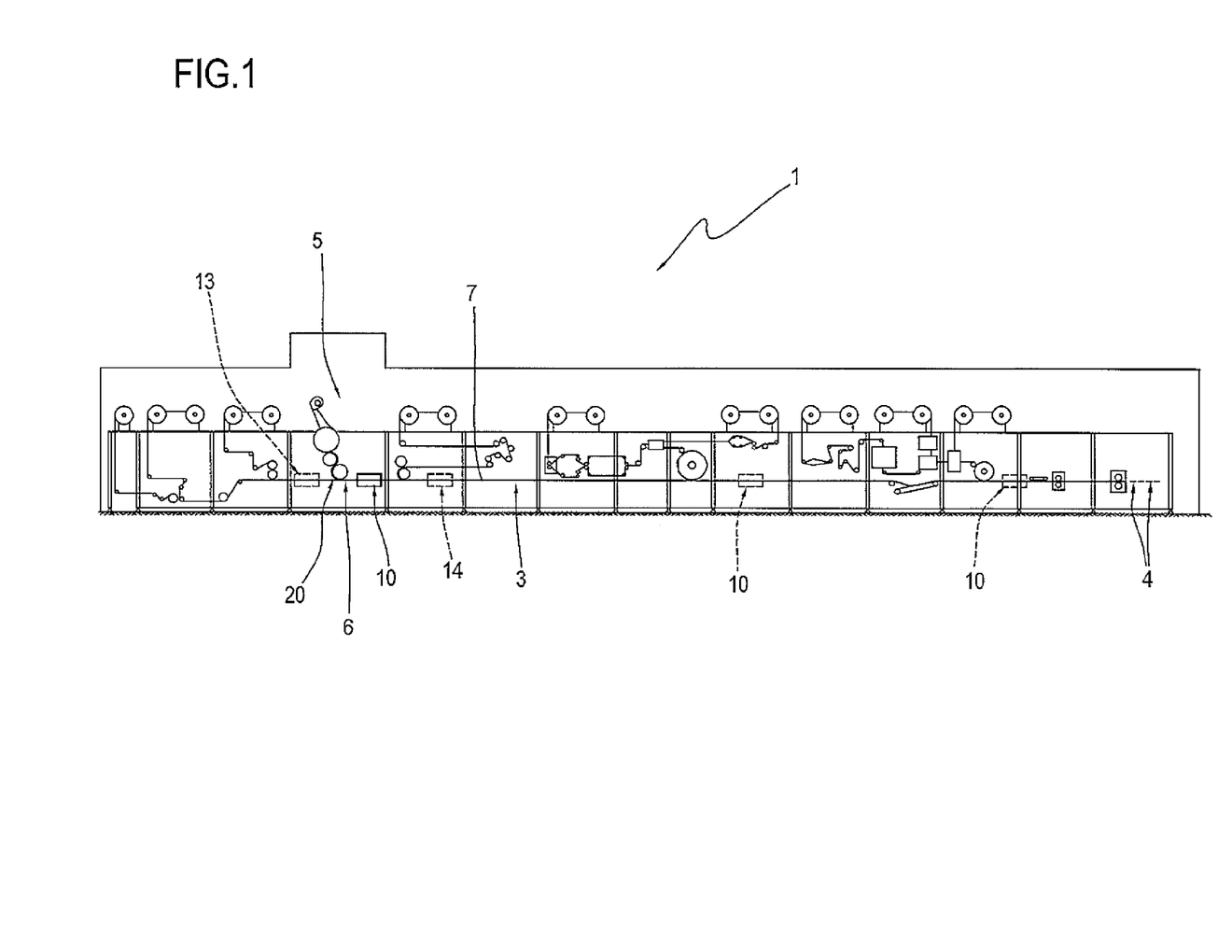
FIG. 1 is a schematic front view illustrating a machine for making absorbent sanitary articles according to this invention.

With reference to FIG. 1, the numeral 1 denotes in its entirety a machine for making absorbent sanitary articles.

An absorbent article 4 comprises a sheet of permeable material and a sheet of impermeable material having, sandwiched between them, an absorbent pad 2 constituting the part of the article whose function is to absorb liquids.

For this purpose, the absorbent pad 2 comprises at least a first absorbent material 8.

In this embodiment, the first absorbent material 8 is made mainly from natural fibre material (fluff) 8a uniformly blended with superabsorbent polymer material ("SAP") 8b.

In this embodiment, the first absorbent material 8 is made mainly or only from natural fibre material (fluff) 8a or superabsorbent polymer material ("SAP") 8b.

To increase its absorbing capacity, the pad 2 also comprises at least one discrete layer 9 of superabsorbent polymer material ("SAP") 9a defining a second absorbent material.

Preferably, the superabsorbent polymer material used is superabsorbent polymer material in granular form.

In the embodiment illustrated in FIG. 1, the absorbent pad 2 comprises a plurality of absorbent materials 8a, 8b, 9a.

Preferably, the "SAP" 8a of the first absorbent material 8 is of the same type as the "SAP" 9a defining the discrete layers 9 of the absorbent pad 2.

Alternatively, the "SAP" 8a of the first absorbent material 8 is of a different type from the "SAP" 9a defining the discrete layers 9 of the absorbent pad 2.

The machine 1 comprises a line 3 for feeding at least one continuous web 7 of impermeable material used to make the above mentioned sheet of impermeable material.

The machine 1 comprises a unit 5 for forming and applying a succession 20 of absorbent pads 2 and located along the feed line 3.

More specifically, the unit 5 is substantially tangent to the feed line 3 at a release station 6.

Depending on the type of absorbent article 4 to be made, the article may comprise different accessory components, such as, for example, elastic bands, faecal barriers and side tabs.

These accessory components are made in respective operating units which are located along the feed line 3 and which feed the respective accessory components to the continuous web 7 of impermeable material.

The position of these operating units is a function of the zone of application of the respective accessory components on the continuous web 7 of impermeable material.

The unit 5 for forming and applying a succession 20 of absorbent pads 2 comprises at least one system 27, 28, 29 for metering a respective absorbent material 8a, 8b, 9a.

The unit 5 comprises a forming drum 36 by which the absorbent pads 2 are formed.

The drum 36 is substantially tangent to the feed line 3.

On its peripheral surface, the drum 36 has one or more suction recesses 38.

The suction recesses 38 are located on the peripheral surface of the drum 36 at a predetermined spacing P.

As the drum 36 rotates, absorbent pads 2 are gradually formed inside respective suction recesses 38 and, once completed, are released onto the feed line 3 by the drum 36 itself.

The forming and application unit 5 comprises a hood 26 for feeding the absorbent materials 8a, 8b, 9a making up the absorbent pad 2.

The hood 26 is mounted in such a way as to peripherally face at least part of the peripheral surface of the drum 36.

More specifically, the unit 5 comprises a first system 27 for metering the natural fibre material (fluff) 8a and a second system 28 for metering the superabsorbent polymer material ("SAP") 8b of the absorbent material 8.

Figure 4:
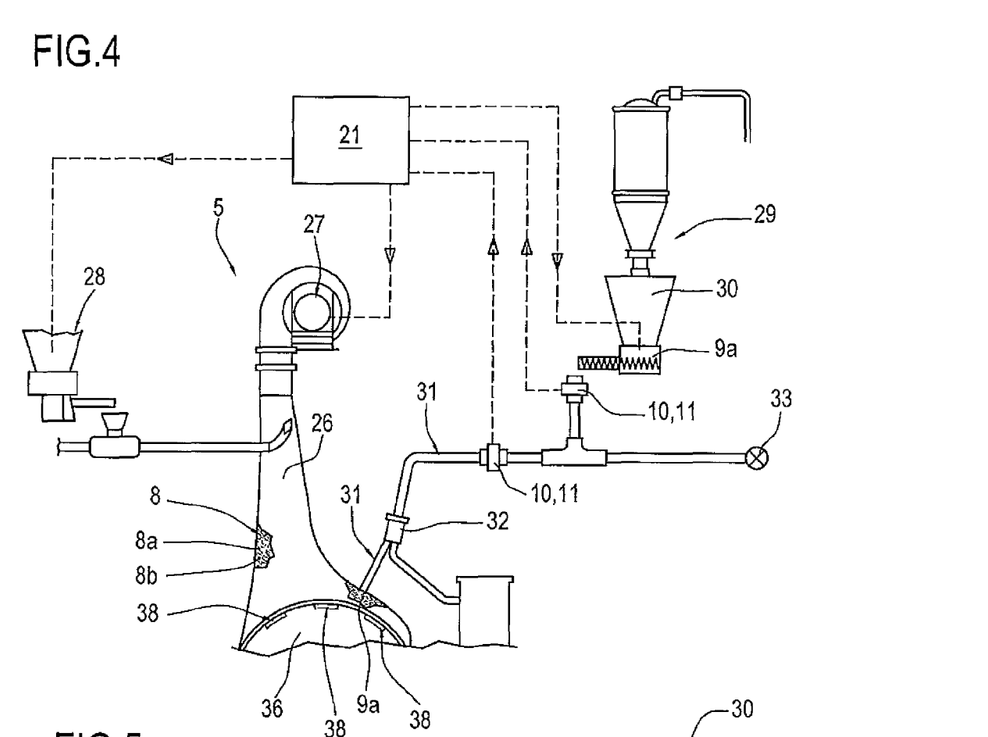
FIG. 4 is a schematic front view of a detail of a third embodiment of the machine of FIG. 1.

The unit 5 also comprises a third system 29 for metering the superabsorbent polymer material ("SAP") 9a defining the discrete layer 9 of the absorbent pad 2, as illustrated in FIG. 4.

The first, second and third metering systems 27, 28, 29 are preferably connected to the feed hood 26.

The third metering system 29 comprises at least one metering device 30 and one feeding duct 31 connected to the metering device 30 at the outfeed of the metering device 30 itself.

The feeding duct 31 comprises, along at least one stretch of it, an intermittent valve 32 defining valve means 32.

The valve means 32 are driven by an actuator unit 37.

The feeding duct 31 is connected to a pressurized air source 33.

The machine 1 comprises a device 10 for detecting at least one between the weight, density profile (or weight profile) parameters of at least one of the absorbent materials 8a, 8b, 9a defining the absorbent pad 2.

Advantageously, the detecting device 10 comprises at least one microwave resonator 11 capable of detecting distinctly one or more absorbent materials 8a, 8b, 9a defining the absorbent pad 2.

In other words, using the detecting device 10 with the microwave resonator 11 it is possible to detect, distinctly from each other, the weights and density profiles (or weight profiles) of the natural fibre material (fluff) 8a, of the superabsorbent polymer material ("SAP") 8b of the absorbent material 8 and of the superabsorbent polymer material ("SAP") 9a defining the discrete layer 9 of the absorbent pad 2.

During its operation, the microwave resonator 11 emits waves at a certain resonance frequency and, depending on the material inspected, generates a certain resonance curve characterized by a resonance frequency and a mean resonance amplitude.

Since each material is characterized by its own resonance curve, having a specific resonance frequency and a specific mean resonance amplitude, the detecting device 10 is capable of detecting and distinguishing each material making up the inspected object and to calculate its weight and/or density profile (or weight profile).

Figure 2:
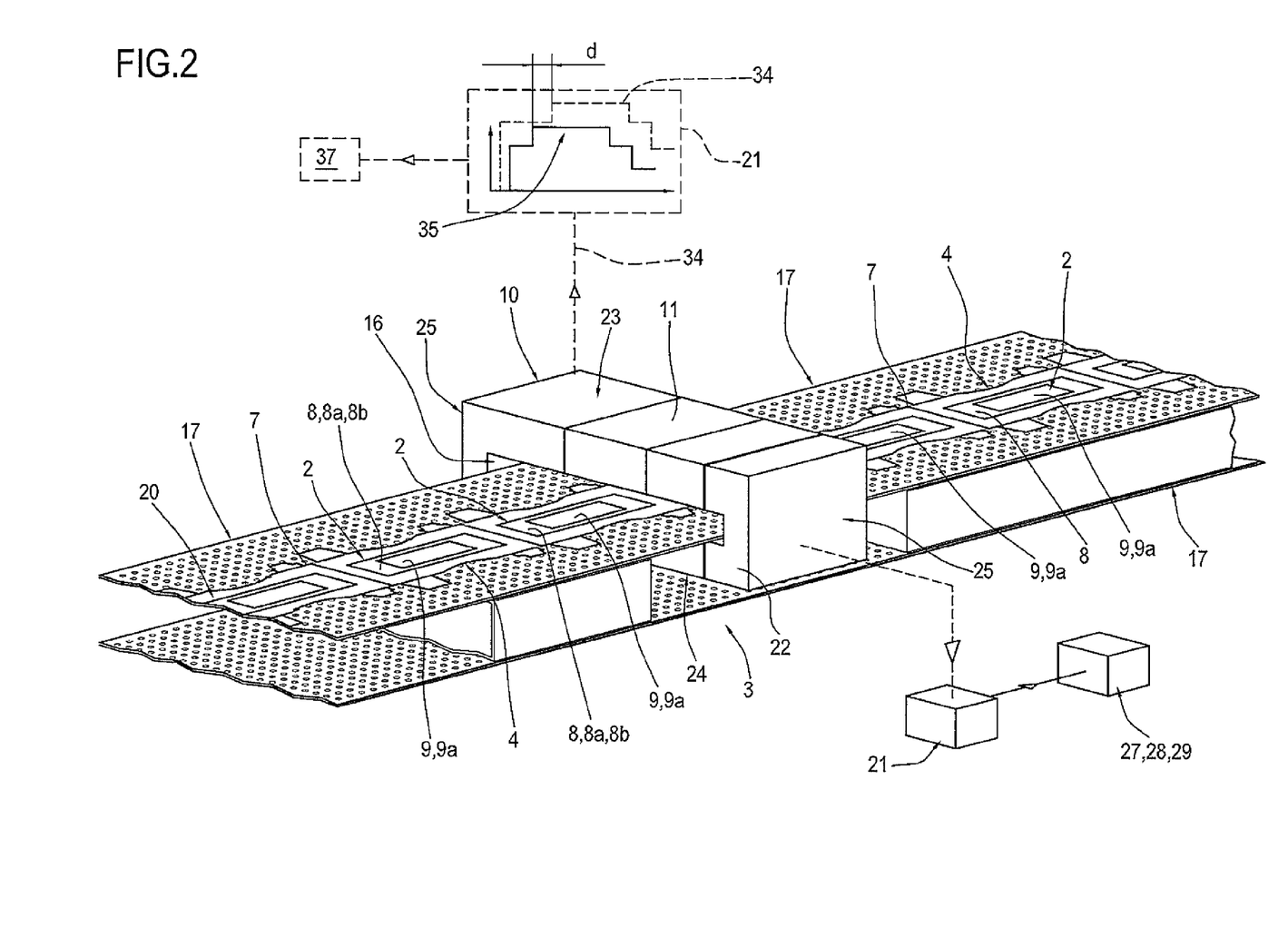
FIG. 2 is a schematic perspective view of a first embodiment of the machine of FIG. 1.
Figure 3:
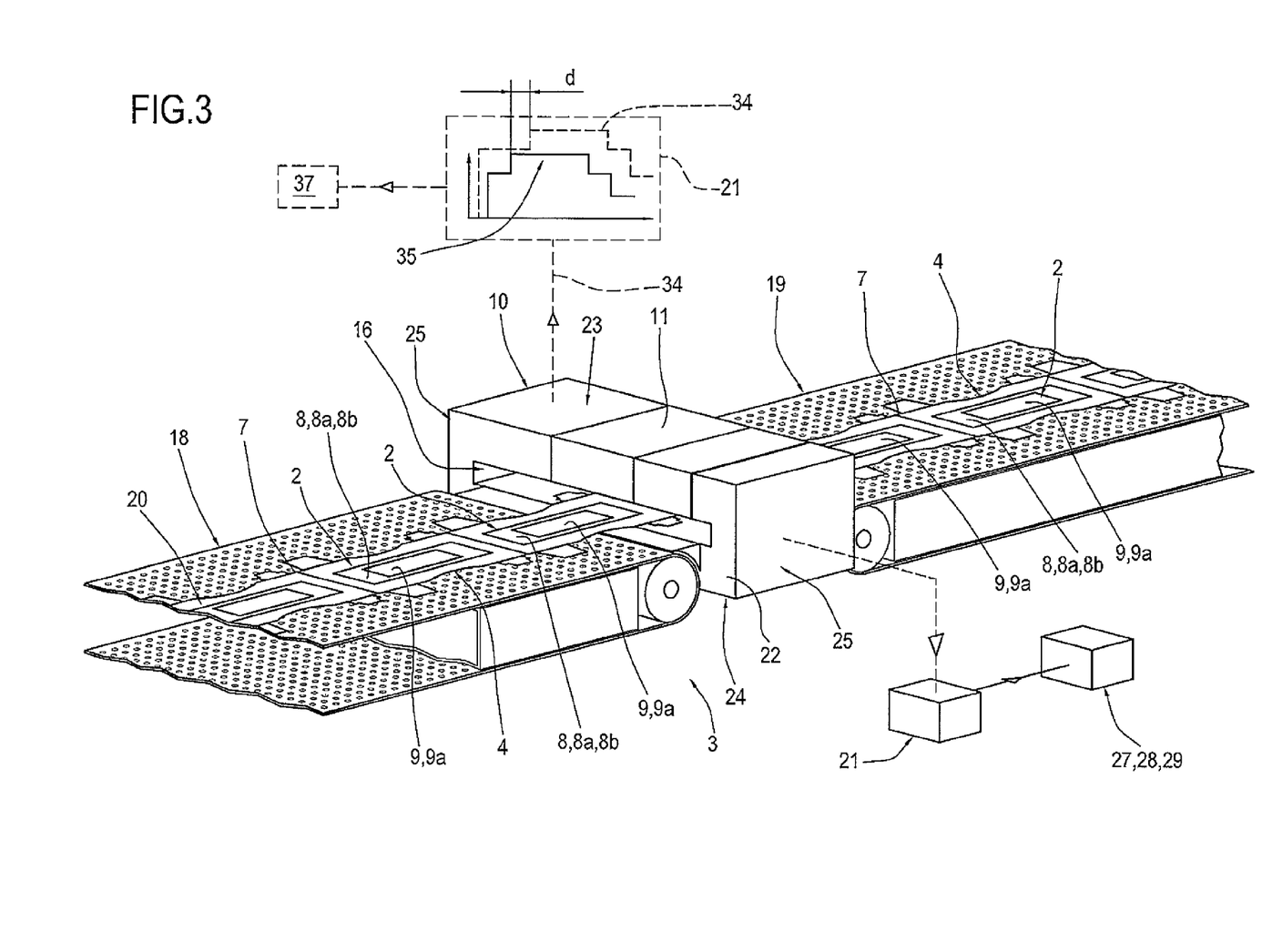
FIG. 3 is a schematic perspective view of a detail of a second embodiment of the machine of FIG. 1.

In a first and a second embodiment of the machine 1, the detecting device 10 is mounted along the feed line 3 downstream of the unit 5 for forming and applying the absorbent pad 2.

In the first and second embodiments of the machine 1, the detecting device 10 is substantially in the shape of a parallelepiped.

The detecting device 10 comprises a top wall 23, a bottom wall 24 and two side walls or flanks 25.

Preferably, the microwave resonator 11 is located at the top wall 23 of the detecting device 10.

The detecting device 10 defines a closed field for the microwave resonator 11.

In order to inspect the absorbent pad 2, the detecting device 10 has a through slot 16 through which at least the succession 20 of absorbent pads 2 runs in a predetermined infeed to outfeed direction.

Preferably, the detecting device 10 is located immediately downstream of the unit 5.

In the first embodiment of the machine 1, as illustrated in FIG. 2, the feed line 3 comprises at least one stretch having a single conveyor belt 17 for conveying the continuous web 7 of impermeable material.

Mounted along that stretch is the detecting device 10, with the conveyor belt 17 and the succession 20 of absorbent pads 2 conveyed thereby running in and out through the slot 16 in the detecting device.

More precisely, and preferably, the detecting device 10 is crossed by the conveyor belt 17, by the continuous web 7 of impermeable material and by the succession 20 of absorbent pads 2.

The microwave resonator 11 is positioned to face and directed towards the conveyor belt 17 and the succession 20 of absorbent pads 2.

More specifically, the microwave resonator 11 is located at the top wall 23 of the detecting device 10.

In the second embodiment, as illustrated in FIG. 3, the feed line 3 comprises at least one stretch having a first and a second conveyor belt 18 and 19 for conveying the continuous web 7 of impermeable material.

The detecting device 10 is interposed between the first and second conveyor belts 18 and 19 in such a way that at least the continuous web 7 of impermeable material and the succession 20 of absorbent pads 2, conveyed by the first and second belts 18 and 19, pass through the detecting device 10.

Thus, the continuous web 7 of impermeable material and the succession 20 of absorbent pads 2 pass in and out through the slot 16 of the detecting device 10.

The microwave resonator 11 is located at the top wall 23 of the detecting device 10 in such a way as to face and be directed towards the continuous web 7 of impermeable material and the succession 20 of absorbent pads 2.

In other words, the second embodiment differs from the first embodiment in that no conveyor belt 18 and 19 transporting the continuous web 7 of impermeable material passes through the detecting device 10.

To allow the detecting device 10 to be mounted easily along the feed line 3, the detecting device 10 comprises at least one removable element 22.

More specifically, once the removable element 22 has been removed, the conveyor belt 17 and/or the continuous web 7 of impermeable material, depending on the embodiment of the machine 1, can be inserted into the slot 16 of the detecting device 10.

Preferably, the removable element 22 defines one of the flanks 25 of the detecting device 10.

It should be noted that to properly inspect the absorbent pad 2, the detecting device 10 must be calibrated to detect only the absorbent materials 8a, 8b, 9a making up the pad 2 itself.

To calibrate the detecting device 10, it is necessary to make the elements to be excluded during detection of the absorbent pad 2 pass through the detecting device 10, such as, for example, the continuous web 7 of impermeable material, the conveyor belt 17 and, if necessary, other accessory components of the absorbent article 4.

The detecting device 10 is preferably calibrated during start-up of the machine 1.

Thus, during the steady-state operation of the machine 1, the detecting device 10 excludes from detection the resonance curves relating to the components of the absorbent article 4 being formed along the feed line 3, with the exception of the absorbent materials 8a, 8b, 9a of the absorbent pad 2.

In an alternative embodiment, to calibrate the detecting device 10, the machine 1 comprises along the feed line 3 at least a first and a second detecting device 13 and 14.

The first detecting device 13 is located upstream of the unit 5 and the second detecting device 14 is located downstream of the unit 5.

The first detecting device 13 is configured to calibrate the second detecting device 14 by detecting all the components of the absorbent article 4 being formed along the feed line 3 to be excluded during detection by the second detecting device 14.

The machine 1 comprises a control and drive unit 21 connected to the detecting device 10.

The control and drive unit 21 is configured to receive from the detecting device 10 at least one between the weight, density profile (or weight profile) parameters of at least one of the absorbent materials 8a, 8b, 9a of the pad 2 and to compare it with a respective reference parameter.

If the parameter detected by the detecting device 10 deviates from the reference parameter by more than a predetermined threshold value, the control and drive unit 21 is configured to drive, as a function of that deviation, the system 27, 28, 29 for metering the respective absorbent material 8a, 8b, 9a.

Advantageously, to check the weight and/or density profile (or weight profile) of the discrete layer 9 of superabsorbent polymer material, the control and drive unit 21 is configured to receive from the detecting device 10 at least one between the weight, density profile (or weight profile) parameters of the superabsorbent polymer material 9a defining the discrete layer 9 and to compare it with a respective reference parameter.

If the parameter detected by the detecting device 10 deviates from the reference parameter by more than a predetermined threshold value, the control and drive unit 21 is configured to drive, as a function of that deviation, the third system 29 for metering the respective superabsorbent polymer material 9a.

The correct contribution in weight of the superabsorbent polymer material 9a defining the discrete absorbent layers 9 is fundamental for guaranteeing effective absorption of liquids by the absorbent pad 2.

If the deviation of the detected parameters from the reference parameters is such that the absorbent pad 2 must be considered defective, the control and drive unit 21 is configured to reject the article comprising the defective absorbent pad 2.

In the first and second embodiments, the detecting device 10 is configured to detect the position 34 of the discrete layer 9 of superabsorbent polymer material 9a inside the absorbent pad 2.

By detected position 34 is meant the density profile, or weight profile, or both profiles of the discrete absorbent layer 9 along a main longitudinal direction of extension of the absorbent pad 2.

The device 10 for detecting the absorbent pad 2 sends the detected position 34 of the discrete layer 9 of superabsorbent polymer material 9a to the control and drive unit 21.

The control and drive unit 21 compares the position 34 detected by the detecting device 10 with a reference position 35 and calculates the deviation "d" between the detected position 34 and the reference position 35.

The control and drive unit 21 is configured to drive the actuator unit 37 and to bring the valve means 32 into phase with the rotation of the forming drum 36 as a function of the deviation "d".

In use, during the passage of the succession 20 of absorbent pads 2 through the slot 16, the detecting device 10 of the second and third embodiments is configured to detect the density profile, or weight profile, or both profiles of the discrete absorbent layer 9, preferably step by step.

More specifically, the detecting device 10 is configured to detect the density profile, or weight profile, or both profiles of the discrete absorbent layer 9 along a main longitudinal direction of extension of the absorbent pad 2.

The density profile, or weight profile, or both profiles of the discrete absorbent layer 9 defines the position 34 detected by the detecting device 10.

The detecting device 10 sends the detected position 34 to the control and drive unit 21 and the latter compares the position 34 with the reference position 35 and calculates its deviation "d".

If the deviation "d" is such that the valve means 32 are no longer in phase with the drum 36, the control and drive unit 21 drives the actuator unit 37 to reset the valve means 32 in phase with the drum 36.

It should be noted that the position 34 detected by the detecting device 10 is the detection signal 34 of the detecting device 10 and the reference position 35 is the reference signal 35 of the detecting device 10.

In a third embodiment, illustrated in FIG. 4, at least one detecting device 10 is mounted along a stretch of the feeding duct 31 downstream of the metering device 30 of the third metering system 29.

Figure 5:
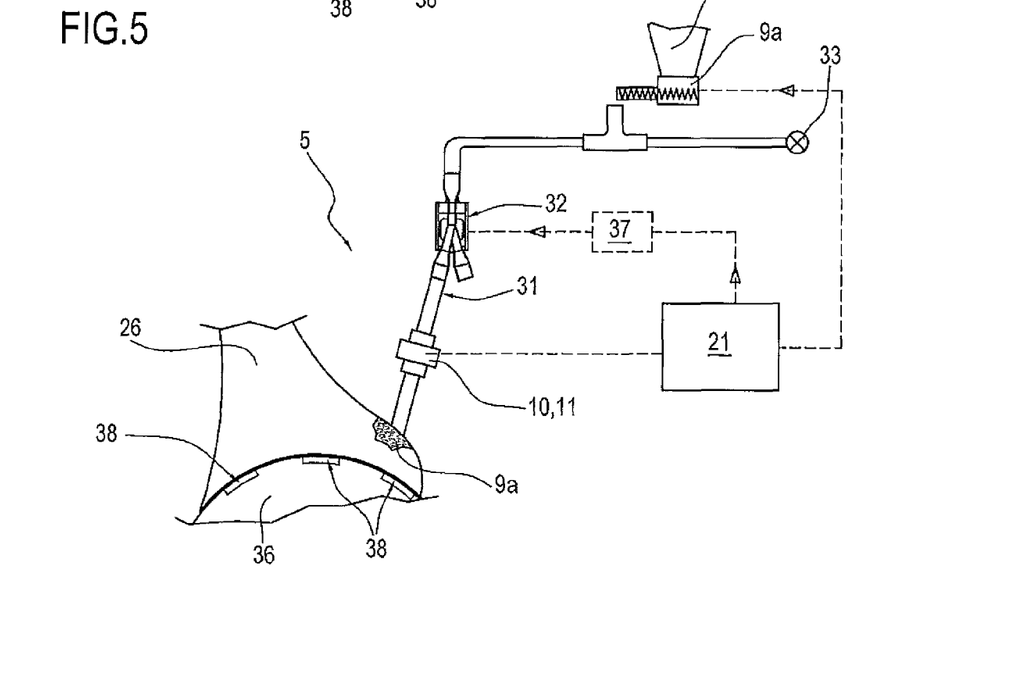
FIG. 5 is a schematic front view of a detail of a fourth embodiment of the machine of FIG. 1.

In a fourth embodiment, illustrated in FIG. 5, at least one detecting device 10 is mounted along the feeding duct 31 downstream of the intermittent valve 32.

In the third and fourth embodiments, the detecting device 10 is substantially tubular in shape so it can be installed along the feeding duct 31.

The microwave resonator 11 is installed in such a way as to be directed towards the inside of the feeding duct 31.

In the third and fourth embodiments, the detecting device 10 detects the weight of one charge of superabsorbent polymer material ("SAP") 9a used to define the discrete absorbent layer 9 of superabsorbent polymer material 9a and sends that parameter to the control and drive unit 21.

The control and drive unit 21 is configured to receive the weight and to compare it with a respective reference weight or reference parameter.

If the weight of the charge of superabsorbent polymer material 9a does not conform with the reference weight, the control and drive unit 21 is configured to operate on the third metering system 29, and more specifically, on the metering device 30, to reset the weight of the charge of superabsorbent polymer material 9a equal to the reference weight.

This invention also relates to a method for making absorbent sanitary articles. More specifically, the method comprises a step of feeding at least one continuous web 7 of impermeable material along a feed line 3, a step of forming and applying a succession 20 of absorbent pads 2 along the continuous web 7 by means of a forming and application unit 5.

The step of forming and applying a succession 20 of absorbent pads 2 comprises a step of feeding a charge of superabsorbent polymer material 9a to a forming drum 36 through a feeding duct 31 comprising valve means 32 driven by a specific actuator unit 37.

The method comprises a step of sending a detection signal 34 indicating that the superabsorbent polymer material 9a has been detected and a step of comparing the detection signal 34 with a reference signal 35.

The method comprises a step of detecting at least one between the weight, density profile (or weight profile) parameters of at least one of the absorbent materials 8a, 8b, 9a defining the absorbent pad 2.

The method further comprises a step of sending at least one between the weight, density profile (or weight profile) parameters of at least one of the absorbent materials 8a, 8b, 9a to a control and drive unit 21 and a step of comparing the detected parameter with a respective reference parameter. A yet further a step of the method comprises driving a system 27, 28, 29 for metering the respective absorbent material as a function of the deviation of the detected parameter from the reference parameter.

The detection step comprises a step of detecting at least one between the weight, density profile (or weight profile) parameters of the superabsorbent polymer material 9a defining the discrete layers 9 of the absorbent pad 2.

The method comprises a step of sending at least one between the weight, density profile (or weight profile) parameters of the superabsorbent polymer material 9a to a control and drive unit 21 and a step of comparing the detected parameter with a respective reference parameter; and a step of sending a feedback drive signal to a system 29 for metering the superabsorbent polymer material 9a defining the discrete layers 9 of the absorbent pad 2 as a function of the deviation of the detected parameter from the reference parameter.

In a first and a second embodiment, the step of detecting at least one between the weight, density profile (or weight profile) parameters of at least one of the absorbent materials 8a, 8b, 9a occurs downstream of the unit 5 for forming and applying the absorbent pad 2.

In a third and a fourth embodiment, the step of detecting at least one between the weight, density profile (or weight profile) parameters of at least one of the absorbent materials 8a, 8b, 9a occurs during the formation of the absorbent pad 2 in the above mentioned unit 5 for forming and applying the succession 20 of absorbent pads 2.

As a function of the deviation between the detection signal 34 and the reference signal 35, the method comprises a step of driving the actuator unit 37 of the valve means 32 into phase with the drum 36.

More specifically, in a first embodiment, the detection signal 34 indicating that the superabsorbent polymer material 9a has been detected is generated when the charge of superabsorbent polymer material 9a passes in the feeding duct 31 downstream of the valve means 32.

The method comprises a step of detecting the density profile, or weight profile, or both profiles of superabsorbent polymer materials (8b, 9a) defining the discrete layers (9); the density profile, or weight profile, or both defining the position (34) of the discrete layer (9) of superabsorbent polymer material (8b, 9a) inside the absorbent pad (2).

The step of detecting the density profile, or weight profile, or both profiles of superabsorbent polymer materials (8b, 9a) defining the discrete layers (9) occurs downstream of the unit (5) for forming and applying the absorbent pad (2).

In a second and a third embodiment, the step of sending a detection signal 34 indicating that the superabsorbent polymer material 9a has been detected comprises a step of detecting the position 35 of the discrete layer 9 of superabsorbent polymer material 9a and a step of comparing the detected position 34 with a reference position 35.

The method comprises a step of driving the actuator unit 37 of the valve means 32 into phase with the drum 36 as a function of the deviation between the detected position 34 and the reference position 35.

Advantageously, unlike inductive sensors used in the prior art, the detecting device 10 comprising a microwave resonator 11 is not affected, in detecting the specified parameters, by external factors such as the temperature and humidity of the operating environment.

Moreover, the microwave resonator 11 allows distinguishing each absorbent material 8a, 8b, 9a defining the pad and to calculate the weight and density profile (or weight profile) of each material.

Advantageously, the detecting device 10 makes it possible to detect whether or not the intermittent valve means 32 are in phase with the forming drum 36 and, if they are not in phase, to reset the actuator unit 37 in phase with the forming drum 36 by means of the control and drive unit 21.

Advantageously, detecting the position of the discrete layer 9 of superabsorbent polymer material 9a constituting the discrete layers 9 of the pad 2 by means of the detecting device 10 allows considerable savings in terms of labour cost because it is no longer necessary for an operator to be present at the end of the feed line 3 to check the correct position of the discrete layer 9.

The invention claimed is:

1. A machine for making absorbent sanitary articles which comprise an absorbent pad in turn comprising one or more absorbent materials, the absorbent pad comprising a discrete layer of superabsorbent polymer material, the machine comprising:
   a feed line for feeding a continuous web of impermeable material and a forming unit for forming and applying a succession of absorbent pads along the continuous web of impermeable material;
   the forming unit comprising:
      a metering system for metering the superabsorbent polymer material defining the at least one discrete layer of the absorbent pad, the metering system comprising a metering device and a feeding duct connected to the metering device at an outfeed of the metering device, the feeding duct comprising, along at least one stretch of the feeding duct, an intermittent valve driven by an actuator unit;
      a forming drum forming the absorbent pads;
   a detecting device for detecting the absorbent pad mounted along the feed line downstream of the forming unit;

the detecting device comprising a microwave resonator configured to detect at least one chosen from a density profile and a weight profile of the superabsorbent polymer material defining the discrete layer; at least one chosen from the density profile and the weight profile defining a position of the discrete layer inside the absorbent pad;

a control and drive unit connected to the detecting device;

the detecting device configured to detect and send a position of the discrete layer to the control and drive unit; the control and drive unit being configured to compare the position of the discrete layer with a reference position and calculate a deviation of the detected position from the reference position; the control and drive unit being configured to drive the actuator unit to bring the intermittent valve into phase with a rotation of the forming drum as a function of the deviation.

2. The machine according to claim 1, wherein the detecting device includes a through slot through which the succession of absorbent pads runs.

3. The machine according to claim 1, wherein the feed line comprises a stretch comprising a single conveyor belt for the continuous web of impermeable material; the detecting device being mounted along the stretch of the feed line and being crossed at least by the single conveyor belt and by the succession of absorbent pads conveyed by the single conveyor belt.

4. The machine according to claim 1, wherein the feed line comprises a stretch equipped with a first conveyor belt and a second conveyor belt, separate from each other, for conveying the continuous web of impermeable material; the detecting device being interposed between the first conveyor belt and the second conveyor belt and being crossed at least by the continuous web of impermeable material and by the succession of absorbent pads conveyed by the continuous web of impermeable material.

5. The machine according to claim 1, wherein the detecting device comprises a removable element which allows the detecting device to be mounted along the feed line.

6. The machine according to claim 1, wherein the microwave resonator at least partly faces the succession of the absorbent pads advancing along the feed line.

7. A method for making absorbent sanitary articles which comprise an absorbent pad in turn comprising one or more absorbent materials, the absorbent pad comprising a discrete layer of superabsorbent polymer material, the machine; the method comprising the following steps:

providing a machine comprising:
a feed line for feeding a continuous web of impermeable material and a forming unit for forming and applying a succession of absorbent pads along the continuous web of impermeable material;

the forming unit comprising:
a metering system for metering the superabsorbent polymer material defining the at least one discrete layer of the absorbent pad, the metering system comprising a metering device and a feeding duct connected to the metering device at an outfeed of the metering device, the feeding duct comprising, along at least one stretch of the feeding duct, an intermittent valve driven by an actuator unit;

a forming drum forming the absorbent pads;

a detecting device for detecting the absorbent pad mounted along the feed line downstream of the forming unit;

the detecting device comprising a microwave resonator configured to detect at least one chosen from a density profile and a weight profile of the superabsorbent polymer material defining the discrete layer; at least one chosen from the density profile and the weight profile defining a position of the discrete layer inside the absorbent pad;

a control and drive unit connected to the detecting device;

the detecting device configured to detect and send a position of the discrete layer to the control and drive unit; the control and drive unit being configured to compare the position of the discrete layer with a reference position and calculate a deviation of the detected position from the reference position; the control and drive unit being configured to drive the actuator unit to bring the intermittent valve into phase with a rotation of the forming drum as a function of the deviation;

feeding the continuous web of impermeable material along the feed line;

forming and applying the succession of absorbent pads along the continuous web of impermeable material via the forming unit;

detecting the at least one chosen from the density profile and the weight profile of the superabsorbent polymer material defining the discrete layer.

8. The method according to claim 7, wherein the step of detecting the at least one chosen from the density profile and the weight profile of superabsorbent polymer material defining the discrete layer occurs downstream of the forming unit.

9. The method according to claim 7 comprising comparing the detected position with a reference position and driving the actuator unit of the intermittent valve into phase with the forming drum as a function of the deviation of the detected position from the reference position.

* * * * *